United States Patent
Ronström

(10) Patent No.: US 8,679,085 B2
(45) Date of Patent: Mar. 25, 2014

(54) REUSABLE DIAPER

(76) Inventor: Iréne Ronström, Västerás (SE)

( * ) Notice: Subject to any disclaimer, the term of this patent is extended or adjusted under 35 U.S.C. 154(b) by 311 days.

(21) Appl. No.: 13/026,444

(22) Filed: Feb. 14, 2011

(65) Prior Publication Data

US 2011/0202030 A1 Aug. 18, 2011

(30) Foreign Application Priority Data

Feb. 16, 2010 (SE) .................................. 1050149

(51) Int. Cl.
*A61F 13/49* (2006.01)
*A61F 13/505* (2006.01)
*A61F 13/74* (2006.01)
*A61F 13/76* (2006.01)

(52) U.S. Cl.
USPC ...... 604/398; 604/385.19; 604/386; 604/393; 604/394; 604/397; 604/385.14

(58) Field of Classification Search
USPC ............. 604/385.01, 385.13–385.16, 385.19, 604/386, 387, 393–399
See application file for complete search history.

(56) References Cited

U.S. PATENT DOCUMENTS

| | | | | | |
|---|---|---|---|---|---|
| 2,141,105 | A | * | 12/1938 | Eller et al. | 604/394 |
| 2,509,674 | A | * | 5/1950 | Cohen | 604/398 |
| 2,545,674 | A | * | 3/1951 | Ralph | 604/394 |
| 2,566,193 | A | * | 8/1951 | Grossman | 604/394 |
| 2,695,025 | A | * | 11/1954 | Andrews | 604/398 |
| 2,832,346 | A | * | 4/1958 | Geneva | 604/398 |
| 3,303,515 | A | * | 2/1967 | Seymour | 2/275 |
| 3,658,064 | A | * | 4/1972 | Pociluyko | 604/360 |
| 4,940,464 | A | * | 7/1990 | Van Gompel et al. | 604/396 |
| 5,360,422 | A | | 11/1994 | Brownlee et al. | |
| 6,605,071 | B1 | * | 8/2003 | Gray et al. | 604/385.28 |
| 2002/0010452 | A1 | | 1/2002 | Dupuy | |
| 2003/0135187 | A1 | * | 7/2003 | Klemp et al. | 604/385.01 |
| 2006/0264862 | A1 | * | 11/2006 | Yoshida et al. | 604/386 |

\* cited by examiner

*Primary Examiner* — Jackie Ho
*Assistant Examiner* — Kathryn E Ditmer
(74) *Attorney, Agent, or Firm* — Dilworth & Barrese, LLP.

(57) ABSTRACT

The present invention relates to a reusable diaper shaped as a pair of pants and designed to house a removable absorbent insect (6). The diaper comprises an elongated central piece (5) impermeable to water and designed to house said insert, and two side pieces (12,13) arranged on opposite sides of the central piece, wherein at least one of the side pieces is made of a material permeable to water and is arranged stretchable to allow stretching of waist and leg openings of the diaper when the diaper is put on and taken off, and the central piece and the side piece are joined together by means of a joint (15,16) forming a liquid barrier.

15 Claims, 3 Drawing Sheets

REUSABLE DIAPER

FIELD OF THE INVENTION

The present invention relates to a reusable diaper shaped as a pair of pants and designed to house a removable absorbent insert.

PRIOR ART

A disadvantage with the disposable diapers used today is that they are not environmentally friendly since they are thrown after they have been used. Further, as the disposable diapers contain plastic material they are not suitable for composting. A diaper has two functions; one is to absorb liquid and the other is to seal against the cloths. From an environmental point of view it is advantageous to instead divide the two functions into two pieces: a removable liquid absorbing insert and a washable diaper shaped as a pair of pants which prevent leakages and keeps the insert in position. The removable insert can be made of a washable material, such as cotton cloth, or be made of a material suitable for composting, such as cellulose.

U.S. Pat. No. 2,141,105 discloses an example of a device for holding an absorbent pad in place on a human body. The holder is opened and closed by means of a pair of zippers. The holder is made from a single piece of a material. The material used in forming the holder is a relatively light elastic material withstanding the chemical actions or excretions to which it may be subjected. As the size of a baby changes and also is different for different babies, the size of the waste and leg openings of the diaper have to be adjustable. In this document the material of the holding device is elastic to enable waste adjustment. However, to seal against the cloths the material has to be impermeable to water. A problem is that is does not exist a material impermeable to water having sufficient elasticity to enable a desired waste adjustment.

US2002/0010452 shows an example of waterproof diaper for infants including a reusable or disposable pad insertable between a permeable inner panel and an impermeable outer panel. The diaper has an hour glass configuration when open and is provided with snap closures arranged to provide waste adjustment. To enable the waste adjustment, the rear part of the diaper holder is provided with a plurality of pairs of snap closures. This diaper holder is suitable for small infants. A problem with this diaper is that it can be difficult to put it on an older mobile child able of walking and running and accordingly not interested in laying down while the diaper is put on. Further disadvantages with this diaper is that it is expensive to produce due to the two panels, the diaper has to be washed after each time it has been used, and it is difficult to button.

U.S. Pat. No. 5,360,422 shows a washable diaper designed to house a removable absorbent insert. The diaper includes two walls and two end pockets for holding the removable insert in place. A disadvantage with this diaper is that it is expensive to produce due to the walls.

OBJECTS AND SUMMARY OF THE INVENTION

The object of the present invention is to provide an improved reusable diaper which for easy to put on for an older children which are up and going, as well as for adults.

This object is achieved by the reusable diaper according to the description herein.

Such a diaper is shaped as a pair of pants and designed to house a removable absorbent insert. The diaper comprises an elongated central piece impermeable to water and designed to house said insert, and two side pieces arranged on opposite sides of the central piece, wherein at least one of the side pieces is made of a material permeable to water and is arranged stretchable to enable stretching of a waist opening of the diaper when the diaper is pulled on and off, and the central piece and the side piece are joined together by means of a joint forming a liquid barrier. The side piece is arranged stretchable to enable stretching of the waist opening and leg opening of the diaper so that the diaper is allowed to be pulled on and off, without being opened in one of its sides.

According to the invention, the diaper has at least one stretchable side piece. Preferably, both side pieces are stretchable. The side piece is at least arranged stretchable in a direction perpendicular to the length axis of the central piece in order to enables adjustment of the waist and leg size of the diaper. The stretchable side piece enables adjustment of the waist size of the diaper and makes it easy for a child or an adult to pull on and take off the diaper by itself.

The joint between the stretchable side piece and the central part is arranged so that it forms a liquid barrier, thereby preventing moisture from spreading from the central piece, which is made of a material impermeable to water and houses the insert, to the side pieces, which are made of a material permeable to water, and accordingly wetting of cloth wear on top of the diaper is prevented. The invention makes it possible to produce a diaper with a stretchable side piece permeable to water with an impermeable central piece housing a wet insert. The fact that the side piece is permeable to water enables the use an elastic material and the use of a zip fastener for opening and closing of the diaper.

Further advantages with the present invention are that diaper is robust and easy and accordingly cheap to produce.

The insert can be reusable and a made of washable material such as cloth, or of a material suitable for composting, such as cellulose.

According to an embodiment of the present invention, at least one of the side pieces is openable and closable. The combination of an openable and closable side and a stretchable side piece makes it easy to change the insert as well as easy to put on and take off the diaper. The stretchable side piece enables adjustment of the waist size of the diaper and makes it easy for a child or an adult to pull on the diaper by itself when the diaper is closed. When the insert is to be changed the diaper is opened.

According to an embodiment of the invention, both sides of the diaper are openable and closable. This makes it possible to fold up the diaper so that it becomes almost flat, and accordingly becomes easy to put on an infant or an adult who is laying down. This embodiment makes it possible to choose between to pull on the diaper in the same way as a pair of pants, or to put on the diaper in the same way as a traditional diaper.

According to an embodiment of the invention, said central piece and the side piece are made of textile materials, and the central piece and the side piece are joined together by means of a water proof seam. An advantage with using textile materials is that the diaper can breathe and stays cooler than the disposable diapers.

According to an embodiment of the invention, said central piece comprises an inner panel and an outer panel, one edge part of said side piece is joined between the outer and inner panel by a first seam, and the outer and inner panels are joined together by a second seam arranged at a distance from said edge part, thereby forming a water proof seam. Such a joint is strong, durable, and easy to produce.

According to an embodiment of the invention, said central piece comprises an inner panel and an outer panel and said inner panel form together with the outer panel a pocket for receiving and retaining an edge part of the insert. The pocket keeps the absorbent insert in place. The same joint is used to fasten the pocket and to achieve the liquid barrier. Thus the number of joints is reduced and accordingly the production of the diaper is simplified.

According to an embodiment of the invention, the outer panel has a length that extends over the entire length of the diaper and the inner panel has a length that corresponds to the length of the water proof seam. Thus, the pocket becomes large enough to hold the insert in position, without the need of any walls, and accordingly the production cost of the diaper is reduced.

According to an embodiment of the invention, said inner panel includes a two panel parts, which together with the outer panel form two pockets for receiving and retaining two opposite edge parts of the insert. The two pockets keep the insert in place.

The diaper is arranged openable and closable by fastening means arranged in at least one of said side pieces. Suitably, the diaper is arranged openable and closable in both of its sides by fastening means arranged in both side pieces. The fastening means can be of different types such as snap members, press buttons, or Velcro© fastening.

According to an embodiment of the invention, the diaper is arranged openable by means of at least one zip fastener arranged in one of said side pieces. A zip fastener is quick and easy to use. A further advantage with a zip fastener is that it is soft and does not rub legs and stomach.

According to an embodiment of the invention, the diaper comprises a first zip fastener arranged in one of said side pieces and a second zip fastener arranged in the other side piece. This embodiment makes it quick and easy to open and close the diaper.

BRIEF DESCRIPTION OF THE DRAWINGS

The invention will now be explained more closely by the description of different embodiments of the invention and with reference to the appended figures.

DETAILED DESCRIPTION OF PREFERRED
EMBODIMENTS OF THE INVENTION

Figure 1:
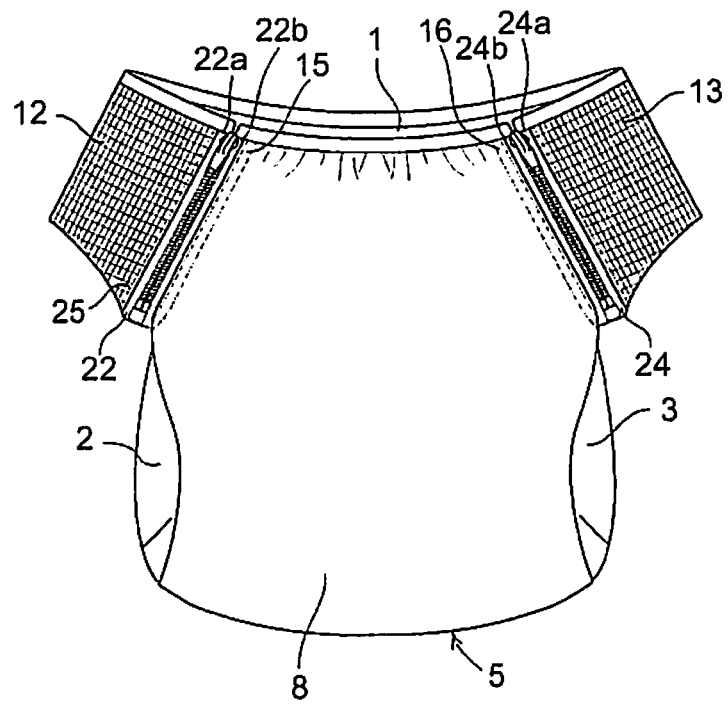
FIG. 1 shows a front view of a diaper according to en embodiment of the invention when the diaper is closed.
Figure 2:
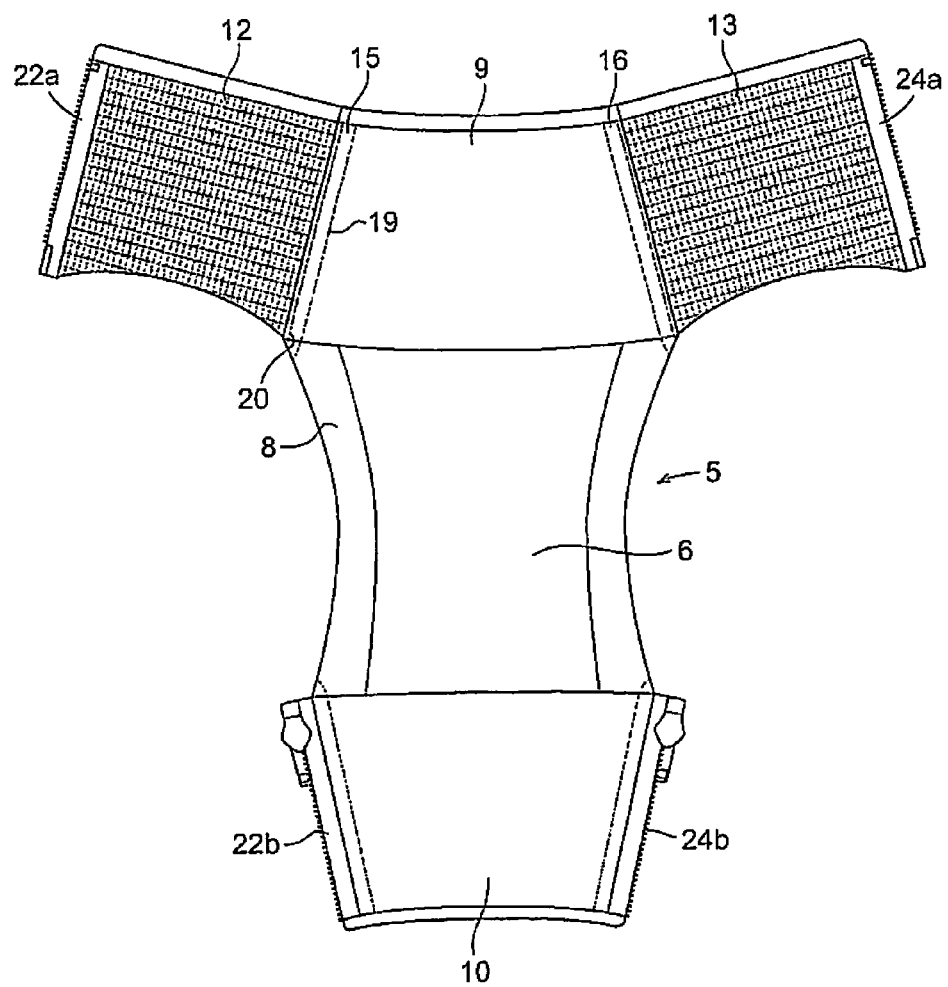
FIG. 2 shows in a view from above the diaper shown in FIG. 1 when it is opened.

FIGS. 1 and 2 show a diaper according to a first embodiment of the invention. FIG. 1 shows the diaper when it is closed and FIG. 2 shows the diaper when it is opened and unfolded. When the diaper is closed it is shaped as of a pair of pants with a large waist opening 1 and two smaller leg openings 2, 3. The diaper includes an elongated central piece 5, designed to house a removable absorbent insert 6. The insert can be reusable or disposable, for example, made of clothes or cellulose. The central piece 5 is mainly rectangular and may have a slight hour glass form when the diaper is open as shown in FIG. 2. The central piece 5 is impermeable to water, and is, for example, made of a knitted or woven textile material laminated with a waterproof membrane which is allowed to breath, such as Gortex®, in order to prevent damp or liquid to be transported to clothes wear on top of the diaper. The central piece 5 is made of a flexible material to enable the diaper be folded and unfolded. As seen from FIG. 2, the central piece 5 comprises an outer panel 8 and two inner panel parts 9,10, which together form two pockets arranged at each end of the central piece. The pockets are designed to receive the edges of the absorbent insert and to keep the insert in place in the diaper. The inner panels 9,10 have an essentially rectangular shape and is preferably made of the same material as the outer panel 8. Each of the inner panels 9,10 has a length, in the length direction of the outer panel, which corresponds to the length of the side pieces, in the same direction, and accordingly to the length of the water proof seam 15,16. The side of the inner panel part facing the waterproof seam has the same length as the side piece facing the same seam.

Two stretchable side pieces 12,13 are arranged on each side of the central piece 5. The two side pieces 12,13 are arranged so that they form the sides of the pants and the central piece are arranged to form the front side and the back side of the pants. The short edges of the central piece 5 form together with the upper sides of the side pieces the waist opening 1, and a part of the long side of the central piece form together with a lower side of the side piece the leg opening. The two side pieces are made of an stretchable material in order to achieve an adjustable waist width and leg widths and accordingly to allow the diaper to be put on and taken off without having to open its sides. The side pieces are arranged such that they at least are stretchable in a direction perpendicular to the length axis of the central piece 5. Suitably, the side pieces are stretchable in several directions. The side pieces can, for example, be made of elastic fabric, an elastic tape/band, a fabric including Lycra, or a fabric provided with inserted rubber bands. Each of the side pieces is essentially rectangular. However, the lower side can be provided with recess in order to fit better to the legs. Each of the side pieces 12,13 are joined to the central piece 5 by means of joints 15,16 forming a liquid barrier. In this example the joint is a waterproof seam. Alternatively, pieces can be glued together, or the joint can be made using an adhesive tape or band.

Figure 3A:
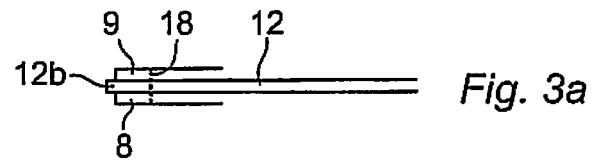
FIGS. 3a-b show an enlargement of the waterproof joint between the side piece and the central piece.
Figure 3B:
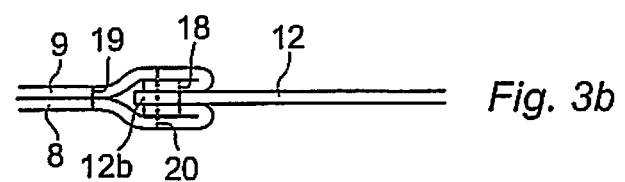

Now, the waterproof seam will be described in more detail with reference to FIGS. 3a-b. FIG. 3a shows the first step of creating the waterproof seam. An edge 12b of the edge piece 12 is arranged between the edges of the inner and outer panels 8,9 of the central piece, such that the edges of the panels are aligned with the edge of the side piece. The edges of the side piece and the outer and inner panels are joined together by a first seam 18. The seam is, for example, sewed with a straight stitch. Then, the outer and inner panels are folded backwards over the seam 18, as shown in FIG. 3b. Thereafter a second seam 19 is sewed at a distance from the edge part 12b of the side piece so that the outer and inner panels 8,9 are joined together. The first and second seam 18,19 are parallel and are sewed along the edge of the side part. Now, the first seam 18 is hidden between the outer and inner panels. Due to the fact that the edge part 12b of the side piece is arranged at a distance from the second seam 19 a liquid barrier is formed between the side piece 12 and the central piece 5. Optionally, a third seam 20 can be made close to and parallel with the seam 18 and joining the side piece and the folded inner and outer panels together, as shown in FIG. 3b, in order to keep the pieces in place. As shown in FIG. 2 the seams 19, 20 are both visible on the outside of the diaper. Both side pieces 12,13 are joined to the central piece by such waterproof seams. The opposite ends of the side pieces are joined to the other end of the central piece.

The first seam 18 keeps the pieces in place relative each other and the second seam 19 keeps the inner and outer panels in place and makes the seam waterproof. The seam prevents leakage between the wet insert and the side pieces including the zip fastener and the stretchable pieces.

In this embodiment, the diaper is openable and closable by means of two zip fasteners 22,24 positioned in the side pieces 12,13. The zip fasteners are arranged in a direction essentially parallel to the length axes of the central part. The zip fastener is preferably made of a plastic material which is soft to the body and can stand many washes. The zip fastener includes two parts 22a-b and 24a-b. One part 22a, 24a of the zip fastener is connected to the side piece 12, 13 by means of a traditional seam 25 and the other part 22b, 24b of the zip fastener is fixedly connected to the central piece 5 by means of the waterproof joint 15,16 described with reference to FIGS. 3a-b. The zip fasteners are arranged so that the diaper is completely openable, which means that when the zip fastener is pulled down it is possible to separate one end of the side pieces from the central piece, which makes it possible to unfold the diaper. In this embodiment both side pieces are provided with zip fasteners. If the child is very movable it can be easier to put on the diaper with the zip fastener closed and with the diaper shaped as a pair of pants. In that case the stretchability of the side pieces are utilized in order to pull on the diaper. An advantage with having a zip fastener in each of the side pieces is that the diaper can be unfolded as shown in FIG. 2. If the child is small and stays still it can be advantageous to open the zip fastener and unfold the diaper before it is put on.

Figure 4:
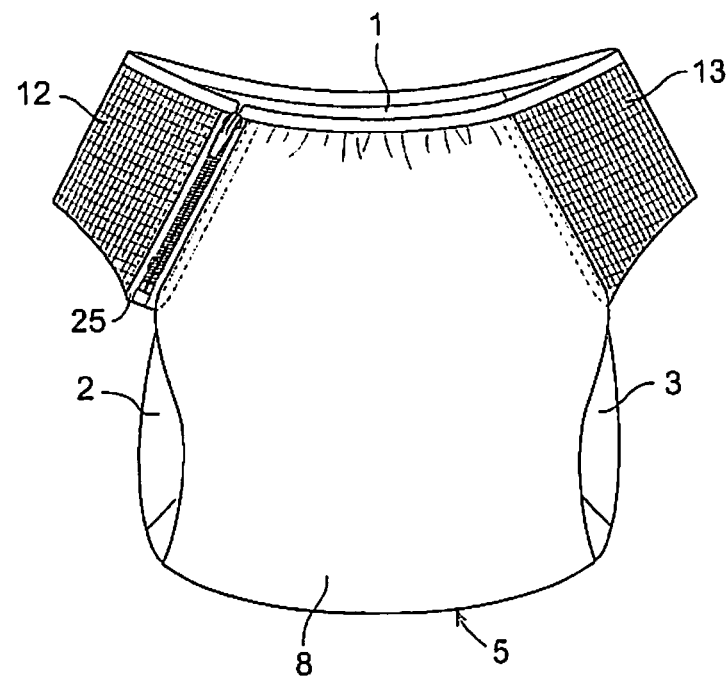
FIG. 4 shows a front view of a diaper according to a second embodiment of the invention.

In an alternative embodiment, the diaper is provided with only one zip fastener. FIG. 4 shows an embodiment in which only one of the side pieces is provided with a zip fastener 25. The other side of the diaper is not openable in this embodiment. When the zip fastener has been pulled up the diaper has the form of a pair of pants. When the zip fastener has been pulled down it is possible to open the diaper in order to facilitate the change of the insert.

Figure 5:
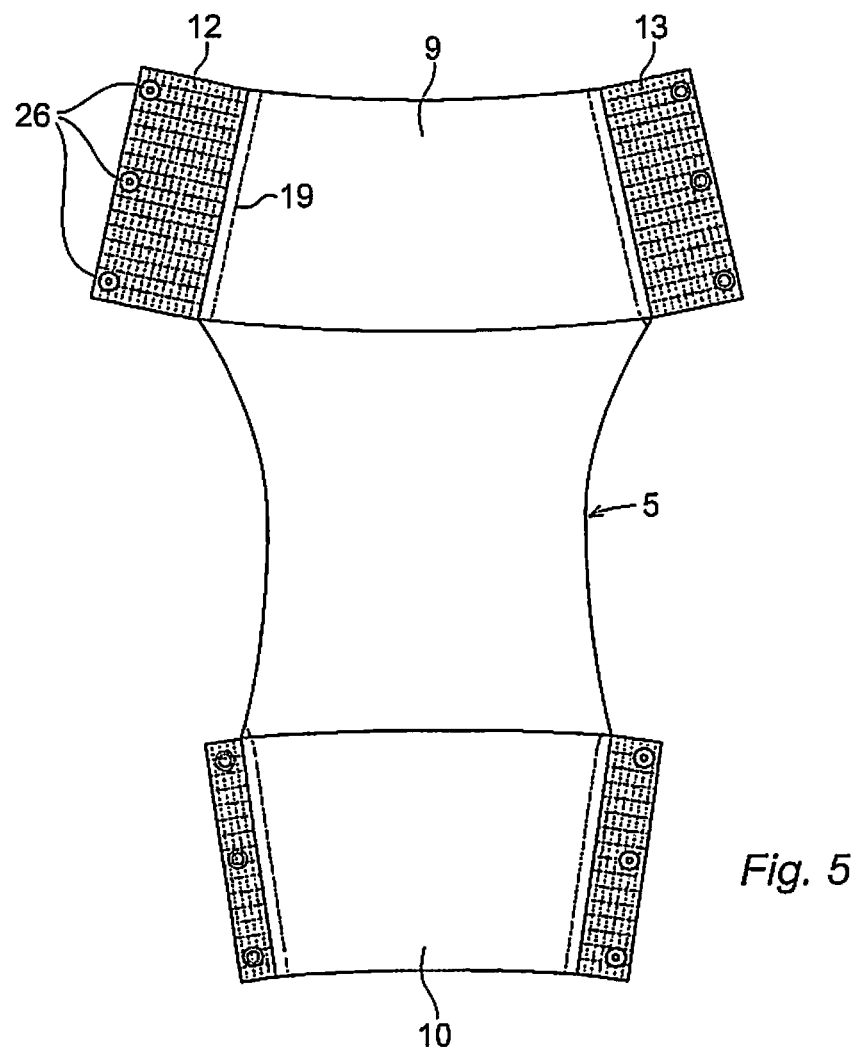
FIG. 5 shows in a view from above a diaper according to a third embodiment of the invention.

FIG. 5 shows a third embodiment of the diaper according to the invention. In this embodiment the fastening means are snap fastener 26 instead of a zip fastener.

The present invention is not limited to the embodiments disclosed but may be varied and modified within the scope of the following claims. For example, other types of fastening means can be used. The surface of the central piece facing outward can be covered with a soft textile material. Further, the zip fastener can be provided in the middle of the side piece or at any other suitable position in the side piece. The invention also covers a diaper which is not openable and closable in any of its sides.

The invention claimed is:

1. A reusable diaper shaped as a pair of pants designed to house a removable absorbent insert (6), wherein the diaper comprises an elongated central piece (5) impermeable to water and designed to house said insert (6), and two side pieces (12,13) arranged on opposite sides of the central piece (5),
   at least one of the side pieces (12, 13) is made of a material permeable to water and arranged stretchable to allow stretching of a waist (1) and a leg (2) opening of the diaper,
   the central piece (5) and the stretchable side piece (12) are joined together by a joint (15,16) forming a liquid barrier,
   said central piece (5) comprises an inner panel (9,10) and an outer panel (8),
   one edge part (12b) of said stretchable side piece (12) is joined between the outer and inner panels (8; 9, 10) by a first sewn seam (18), and
   the outer and inner panels (8; 9, 10) are joined together by a second sewn seam (19) arranged at a distance from said edge part (12b) of the stretchable side piece (12), thereby forming a waterproof seam (15, 16);
   wherein the respective outer and inner panels (8; 9, 10) are folded over the first sewn seam (18) and extend to the second sewn seam (19), with the first sewn seam (18) hidden between the respective outer and inner panels (8; 9, 10).

2. The diaper according to claim 1, wherein said inner panel (9, 10) forms together with the outer panel (8), a pocket for receiving and retaining an edge part of the insert (6).

3. The diaper according to claim 2, wherein the outer panel (8) has a length that extends over the entire length of the diaper and the inner panel (9, 10) has a length that corresponds to the length of said waterproof seam (15, 16).

4. The diaper according to claim 3, wherein said inner panel (9,10) includes a two separate panel parts (9, 10), which together with the outer panel (8) form two separate, pockets for receiving and retaining two opposite edge parts of the insert (6).

5. The diaper according to claim 2, wherein said inner panel (9,10) includes two separate panel parts (9, 10), which together with the outer panel (8) form two separate pockets for receiving and retaining two opposite edge parts of the insert (6).

6. The diaper according to claim 5, wherein said central piece (5) is mainly rectangular and has a slight hourglass form when the diaper is open.

7. The diaper according to claim 1, wherein the diaper is openable and closable in at least one of its sides.

8. The diaper according to claim 1, wherein the diaper is arranged openable and closable by at least one zip fastener (22,24) arranged in one of said side pieces (12,13).

9. The diaper according to claim 8, wherein the diaper comprises a first zip fastener (22) arranged in one of said side pieces (12) and a second zip fastener (24) arranged in the other side piece (13).

10. The diaper according to claim 9, wherein the first and second zip fasteners (22, 24) each comprise first (22a, 24a) and second (22b, 24b) parts, and additionally comprising
    traditional seams (25) each connecting one of the first parts (22a, 24a) of the first and second zip fasteners (22, 24) to one of the side pieces (12, 13), and
    two further waterproof seams (15, 16) each connecting one of the second parts (22b, 24b) of the first and second zip fasteners (22, 24) to the central piece (5).

11. The diaper according to claim 8, wherein only one (12) of the side pieces (12, 13) is provided with a zip fastener (25).

12. The diaper according to claim 1, wherein said at least one stretchable side piece (12) is arranged stretchable in a direction perpendicular to the length axis of the central piece (5).

13. The diaper according to claim 1, wherein both side pieces (12, 13) are made of a material permeable to water and are arranged stretchable to allow stretching of the waist (1) and leg (2,3) openings of the diaper, and each of the side pieces (12, 13) are joined to the central piece (5) by a joint (15,16) forming a liquid barrier.

14. The diaper according to claim 1, additionally comprising a third sewn seam (20) situated parallel and adjacent to the first sewn seam (18) and additionally joining said edge part (12*b*) of said stretchable side piece (12) between said outer and inner panels (8, 9; 10) and folded over portions of said outer and inner panels (8, 9; 10) altogether.

15. The diaper according to claim 1, wherein the diaper is arranged openable and closable by snap fasteners (26) arranged on the side pieces (12, 13) and the inner panel (9, 10) remote from the side pieces (12, 13).

* * * * *